(12) United States Patent  
Adrian

(10) Patent No.: US 6,516,655 B1  
(45) Date of Patent: Feb. 11, 2003

(54) DEVICE AND METHOD FOR TESTING SHEET METAL DEFORMATION

(75) Inventor: Steve Adrian, London, OH (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/086,353

(22) Filed: Mar. 1, 2002

(51) Int. Cl.$^7$ .............................. G01N 3/48; G01N 3/42
(52) U.S. Cl. ....................... 73/83; 73/81; 73/82; 73/85; 73/760; 73/788
(58) Field of Search ........................... 73/81–87

(56) References Cited

U.S. PATENT DOCUMENTS

| 3,657,921 | A | * | 4/1972 | Lang ............................ 73/81 |
| 4,298,308 | A | * | 11/1981 | Richter ....................... 318/488 |
| 4,535,623 | A | * | 8/1985 | Gilberto ........................ 73/81 |
| 4,627,297 | A |   | 12/1986 | Akimoto ................ 73/862.324 |
| 4,852,397 | A | * | 8/1989 | Haggag ......................... 73/82 |
| 4,924,709 | A |   | 5/1990 | Plyter ......................... 73/829 |
| 5,490,416 | A | * | 2/1996 | Adler ............................ 73/82 |
| 6,082,201 | A |   | 7/2000 | Ishikawa ..................... 73/849 |
| 6,247,355 | B1 |   | 6/2001 | Suresh et al. ................. 73/82 |

* cited by examiner

Primary Examiner—Hezron Williams  
Assistant Examiner—David Rogers  
(74) Attorney, Agent, or Firm—Rankin, Hill, Porter & Clark LLP; Alan T. McDonald; Vincent Ciamacco

(57) ABSTRACT

A method and device for testing a metal part for weakness to deformation. The device includes a motor that moves a shaft and a load applicator toward and away from a part being tested. The motor is activated in accordance with a predetermined sequence and in dependence upon pressure sensed by a load cell associated with the shaft. In the method, displacement is measured by a displacement measuring device throughout the testing sequence in order to determine the part's resistance to deformation.

9 Claims, 4 Drawing Sheets

DEVICE AND METHOD FOR TESTING SHEET METAL DEFORMATION

BACKGROUND OF THE INVENTION

1. Field of the Invention

The present invention generally relates to testing equipment and methods and, more particularly, toward a method and device for testing deformation of sheet metal parts.

2. Description of Related Art

In stamping processes to form metal parts, such as automobile body panels, various stamping parameters may have an effect on the resulting metal parts' strength or resistance to deformation. For example, the cushion or stamping pressure used in forming the metal part is directly related to the resistance to deformation of the metal part. However, the optimum cushion pressure, as it relates to deformation resistance, is variable and depends upon many factors, including the curvature or profile of the metal part. Moreover, other factors, such as the location and distribution of internal body panel supports, have a significant affect on the body panel's resistance to deformation. Therefore, it is desirable to test the body panels at various locations to determine their resistance to deformation. In the past, testing for resistance to deformation has been a manual operation whereby a worker applies a predetermined load and visually determines the resulting deformation. As such, the conventional method is inherently inexact, and provides results that vary from worker to worker.

Other methods and devices for testing metal parts have been developed, typically for small parts that are intended to have a certain elasticity, such as flexible electrical contacts. For example, U.S. Pat. No. 6,082,201 teaches a method and device for imposing a predetermined amount of permanent deformation on a heat treated part. The '201 patent teaches placing the flexible contact in a testing jig, contacting a manually-operated load imposer on the flexible contact to establish a set point, and then manually moving the load imposer toward the flexible contact to deform the flexible contact. A displacement measuring unit measures the amount the load imposer is displaced and, when a predetermined amount of displacement is measured, the movement of the load imposer is terminated and the flexible contact, while being held in the deformed condition by the load imposer, is subjected to heat treating.

Following heat treating, the '201 load imposer is manually rotated to release pressure on the flexible contact and, when the load imposer is disconnected from the flexible contact, an final set point is determined. The difference between the initial set point and the final set point is the amount of permanent deformation resulting from the heat treating.

Accordingly, there exists a need in the art for a method and device for automatically testing a sheet metal part to determine the part's resistance to deformation. There further exists a need in the art for a method and device for testing metal parts to detect localized weaknesses.

SUMMARY OF THE INVENTION

The present invention is directed toward a method and device for testing sheet metal parts to determine the part's resistance to deformation. The present invention is further directed toward a method and device for detecting localized weakness in metal parts as part of an overall method for identifying areas requiring remedial strengthening measures.

In accordance with the present invention, a device for testing a metal part for deformation includes a support, a motor secured to the support, a shaft that is moved longitudinally by the motor, a load cell for detecting pressure applied to the metal part, a displacement measuring device for measuring deformation of the metal part, and a controller. The shaft has a dimple head secured thereto for engagement with the metal part. The controller activates the motor to move the dimple head toward and away from the metal part based upon pressure sensed by the load cell.

In further accordance with the present invention, a method for testing a sheet metal part for deformation includes moving a dimple head forwardly toward a test point on the metal part, determining when the dimple head encounters resistance to movement, and measuring displacement of the dimple head when resistance to movement is encountered to establish a first reference displacement value. The dimple head is moved forwardly into the metal part until a predetermined pressure is detected. The displacement of the dimple head when the predetermined pressure is detected is measured to establish a second reference displacement value. Maximum deformation of the metal part at the test point is calculated by subtracting the first reference displacement value from the second reference displacement value.

In further accordance with the inventive method, after the predetermined pressure is detected, the dimple head is moved rearwardly and displacement of the dimple head is measured as the dimple head is moved rearwardly. When the displacement is less than or equal to the first reference displacement value, the dimple head is again moved forwardly. Thereafter, it is determined when the dimple head encounters resistance to movement and the displacement of the dimple head when resistance to movement is encountered is measured to establish a third reference displacement value. A permanent deformation value of the metal part at the test point is determined by subtracting the first reference displacement value from the third reference displacement value.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
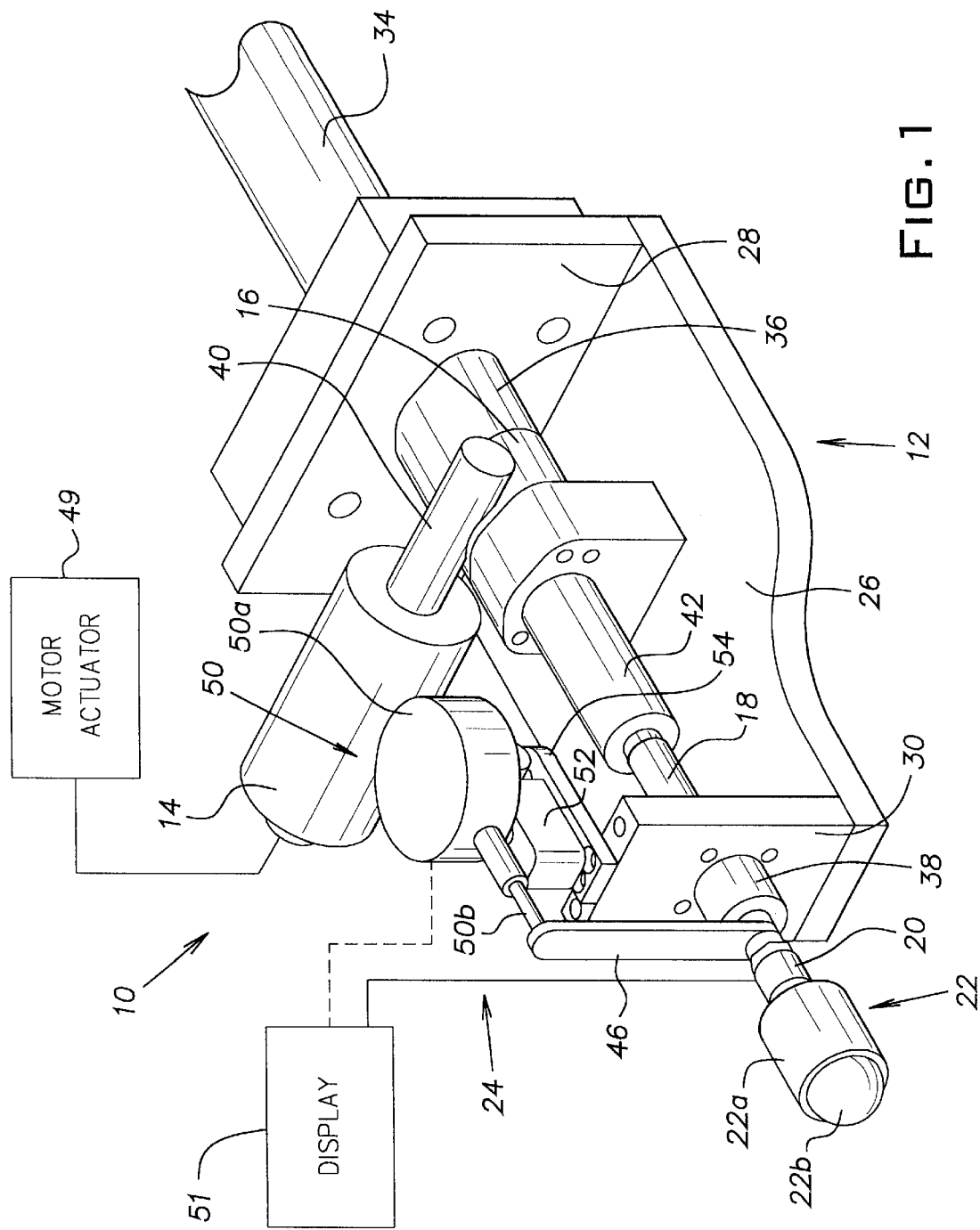
FIG. 1 is a perspective view of a device for testing metal parts according to a first embodiment of the present invention.
Figure 3:
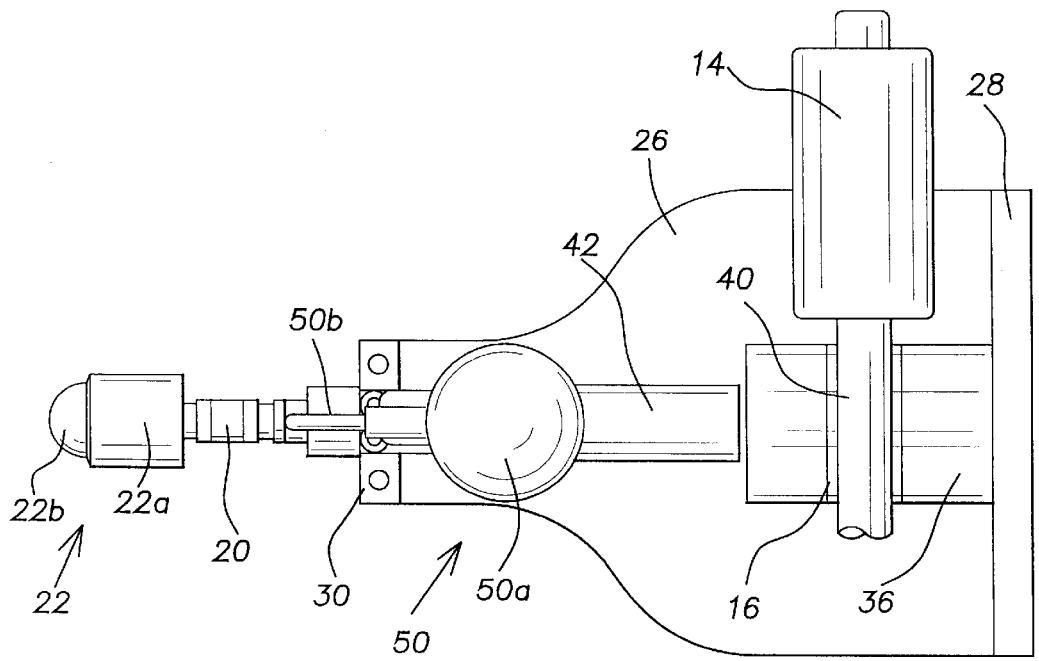
FIG. 3 is a top plan view of the device.
Figure 2:
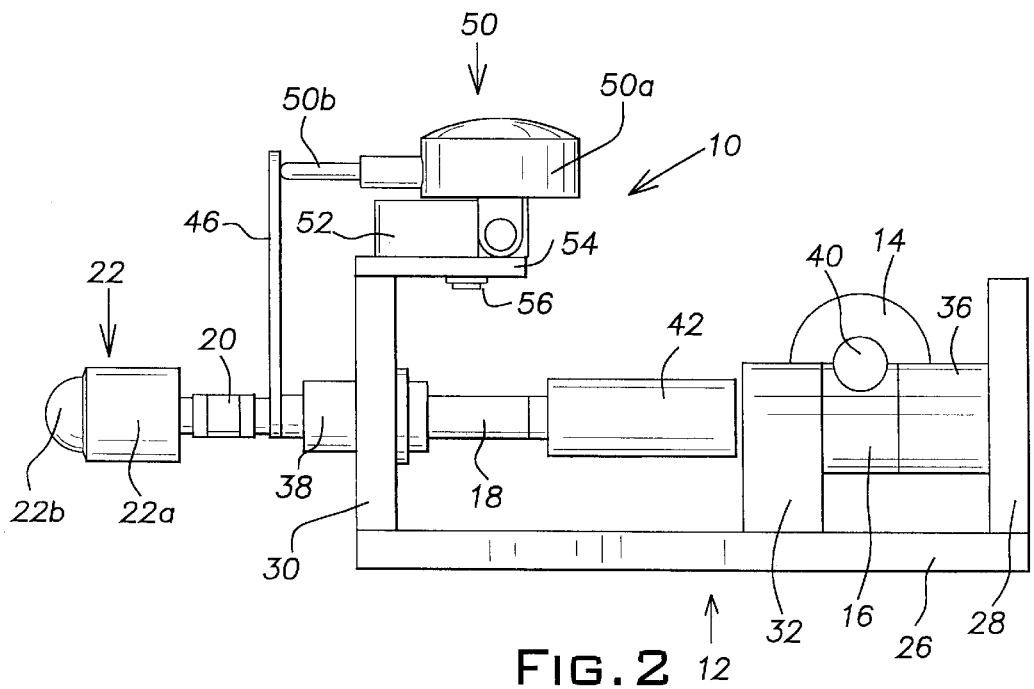
FIG. 2 is a side elevational of the device.
Figure 4:
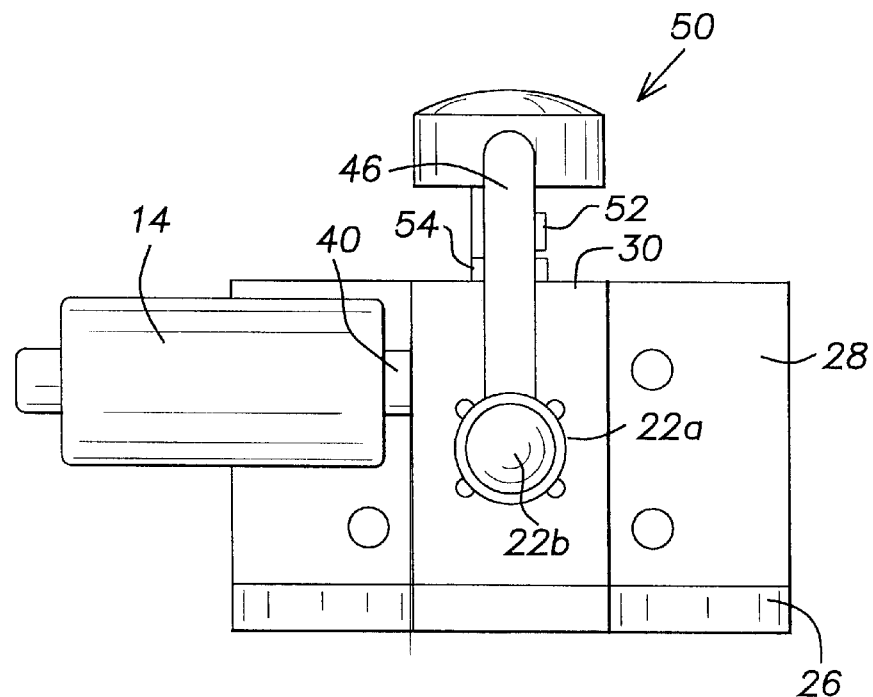
FIG. 4 is a front elevational view of the device.

With reference to FIGS. 1–4, a sheet metal deformation testing device 10 according to the present invention is illustrated. The device 10 includes a support or mounting fixture 12, a motor 14, a worm gear 16, a shaft 18, a load cell 20, a load applicator or dimple head 22, and a displacement detection assembly 24. The mounting fixture 12 includes a base plate 26, a rear plate 28, and a front plate 30. The base plate 26 has the rear plate 28, the front plate 30, and a center support 32 secured thereto.

The rear plate 28 extends upwardly from a first or rearward end of the base plate 26 and includes mounting apertures by means of which the testing device 10 is mounted to a movable arm 34, such as a robot arm, to facilitate placement and movement of the testing device. The rear plate 28 also has a rear support 36 secured thereto, as illustrated.

The front plate 30 extends upwardly from a forward end of the base plate 26 and defines a central opening through which the shaft 18 extends. More specifically, a shaft bearing 38 extends through the central opening in the front plate 30 and slidably receives the shaft 18. The displacement detection assembly 24 is secured to an upper surface of the front plate 30 and extends rearwardly therefrom, as illustrated.

The worm gear 16 is mounted between the rear support 36 and the center support 32 and rotatably engages a drive shaft 40 of the motor 14. The motor 14, which is preferably a dc motor 14, extends laterally from the worm gear 16 and generally transverse to an axis of the shaft 18. The worm gear 16 includes a screw (not shown) that extends through the center support 32 and is rotatably received in a threaded collar 42 that extends forwardly from the center support 32. The threaded collar 42 is affixed to the center support 32 and receives a first end of the shaft 18.

The screw is secured to a first or proximal end of the shaft 18 such that, as the screw is rotated to move forwardly and rearwardly, the shaft 18 is correspondingly slid forwardly and rearwardly. For example, the proximal end of the shaft 18 may be slotted and pinned to a distal end of the screw such that, while the shaft 18 does not rotate, axial movement of the screw forces the shaft 18 to move axially. Since numerous equivalent means for translating axial rotary motion of the screw into axial sliding motion of the shaft 18 are known in the art, the present invention will not be limited to the connection between the screw and shaft 18 specifically disclosed herein.

The shaft 18 extends forwardly through the shaft bearing 38 and is secured, at a second or distal end, to a load cell 20. The load cell 20 is operable to sense pressure developed during use of the device 10, and to transmit pressure data to a display 51 (FIG. 1) and/or a programmable controller 47, which is described hereinafter in the second embodiment of the invention illustrated in FIG. 6. A connector arm 46 of the displacement detection assembly 24 is secured over the shaft 18 and relatively between the shaft bearing 38 and the load cell 20 and moves forwardly and rearwardly with the shaft 18, as will be described more fully hereinafter.

A forward end of the load cell 20 is secured to the dimple head 22. The dimple head 22 includes a body portion 22a and a distal end 22b, the distal end 22b being adapted to simulate particular surface engagement profiles. The distal end 22b is preferably interchangeable to permit different surface engagement profiles to be tested. For example, the illustrated dimple head 22 has a curved or semi-spherical distal end 22b, and is formed from steel. Alternatively, the distal end 22b may have a similarly curved shape, but be formed of a firm rubber material. Naturally, the shape or diameter of the distal end 22b may be freely selected.

The displacement detection assembly 24 includes the connector arm 46, a displacement measuring device 50, a slide block 52, and a mounting arm 54. The displacement measuring device 50 includes an indicator 50a and an extending probe 50b. The probe 50b has a distal end that engages the connector arm 46 and moves forwardly and rearwardly upon corresponding movement of the connector arm 46 (i.e., the shaft 18 and dimple head 22). Movement of the probe 50b is translated by the indicator 50a into measurement information, as is well known to one skilled in such displacement measuring devices.

The indicator 50a may be a dial-type indicator or an electronic-type indicator. Alternatively, the measurement information may be conveniently displayed on the display 51 with the load cell data, described hereinbefore, as shown by the dashed line in FIG. 1. In an automated process, the measurement information will be provided to the programmable controller 47, which is used in the second embodiment to be described hereinafter with reference to FIG. 6, to facilitate control of the device 10 in the testing procedure as well as the compilation of testing data for further analysis.

A first or forward end of the mounting arm 54 is rigidly secured to the upper surface of the front plate 30 and extends rearwardly therefrom. The mounting arm 54 has a slotted opening extending along its length that receives the slide block 52. More specifically, the slide block 52, which has the indicator 50a secured thereto, is disposed on top of the mounting arm 54 and has a slide portion that is slidably received in the slotted opening of the mounting arm 54. A screw 56 extends upwardly through the slotted opening and into a threaded hole in the slide of the slide block 52. The screw 56 clamps the slide block 52 in a desired position on the mounting arm 54. Accordingly, the displacement measuring device 50 is moved with the slide block 52 to a desired position such that the probe 50b is located in a preferred operating position relative to the connector arm 46. The preferred position is one in which the probe 50b is touching the connector arm 46 and wherein the probe stroke is sufficient to permit measuring of displacement throughout the expected travel of the shaft 18 and dimple head 22.

The sheet metal deformation testing device 10 according to the first embodiment of the invention is controlled manually by an operator. For manual operation a motor actuator 49 is used by the operator to activate the motor 14 to drive the shaft 18, and the associated dimple head 22, toward and away from the sheet metal part being tested.

To test a body panel (BP, FIG. 5), the operator will place the dimple head adjacent a first test point, and will activate the motor 14 via the motor actuator 49 to drive the dimple head 22 into contact with the test point. Displacement measured by the displacement measuring device 50 when the load cell 38 measures resistance to movement will be recognized and recorded by the operator as a first reference displacement value ($DV_1$, FIG. 5). Naturally, the operator may reset or "zero" the indicator 50a at the first reference displacement value to serve as a reference point for further measurements. In any event, following recordation of the first reference displacement value the operator will continue to activate the motor 14 to drive the dimple head 22 into the body panel until a predetermined force is measured by the load cell 38.

In successful tests conducted by the inventors, it has been found that setting the predetermined force to 20 kg is satisfactory for the particular body panels that were the subject of the tests. Naturally, it is contemplated that the predetermined force will be variable and depend greatly upon the metal part being tested, particularly the thickness of the metal part, as well as the forces that are expected to commonly confront the body panel during use.

The displacement measured by the displacement measuring device 50 at the predetermined force is recorded by the operator as a second reference displacement value ($DV_2$, FIG. 5), with the difference between the first and second displacement values being a maximum deflection ($D_M$, FIG. 5), which is one measure of the body panel's resistance to deformation at the test point. Thereafter, the operator actuates the motor 14 to move the dimple head 22 away from the body panel. The operator monitors the displacement reading on the indicator 50a or 51 of the displacement measuring device 50 and, when the dimple head 22 has moved rearwardly slightly from the first reference displacement value (i.e., the location at which the body panel was first engaged by the dimple head 22), the operator reverses the motor operation to drive the dimple head 22 toward and into the body panel.

The operator monitors the load cell display 50a or 51 as the dimple head 22 is moved toward the body panel. When the load cell display 50a or 51 indicates resistance to movement, which is indicative of the dimple head 22 engaging the deformed body panel surface, the operator records the displacement value provided by the displacement measuring device indicator 50a or, 51. This reading serves as a third reference value ($DV_3$, FIG. 5). The difference between the first and third reference values is the amount of permanent deformation ($D_P$, FIG. 5) experienced at the body panel first test point due to the predetermined load. The testing procedure on the first test point is complete, and the operator will actuate the motor to withdraw the dimple head 22 from engagement with the body panel and will move the testing device 10 to subsequent testing points for further testing procedures.

During each testing procedure, the operator monitors the load cell display 51 to determine whether snap-through or "oil-canning", which is when the dimple head 22 has penetrated the body panel, has occurred. A sharp drop in pressure sensed by the load cell 20 during initial movement of the dimple head 22 into the body panel (i.e., during application of the predetermined force) is indicative of such snap-through, and will be recorded by the operator as a gross failure (ST, FIG. 5) of the body panel at the subject test point. In the tests conducted by the inventors, a pressure drop of about 1.2 kg was found to be indicative of such snap-through.

Figure 6:
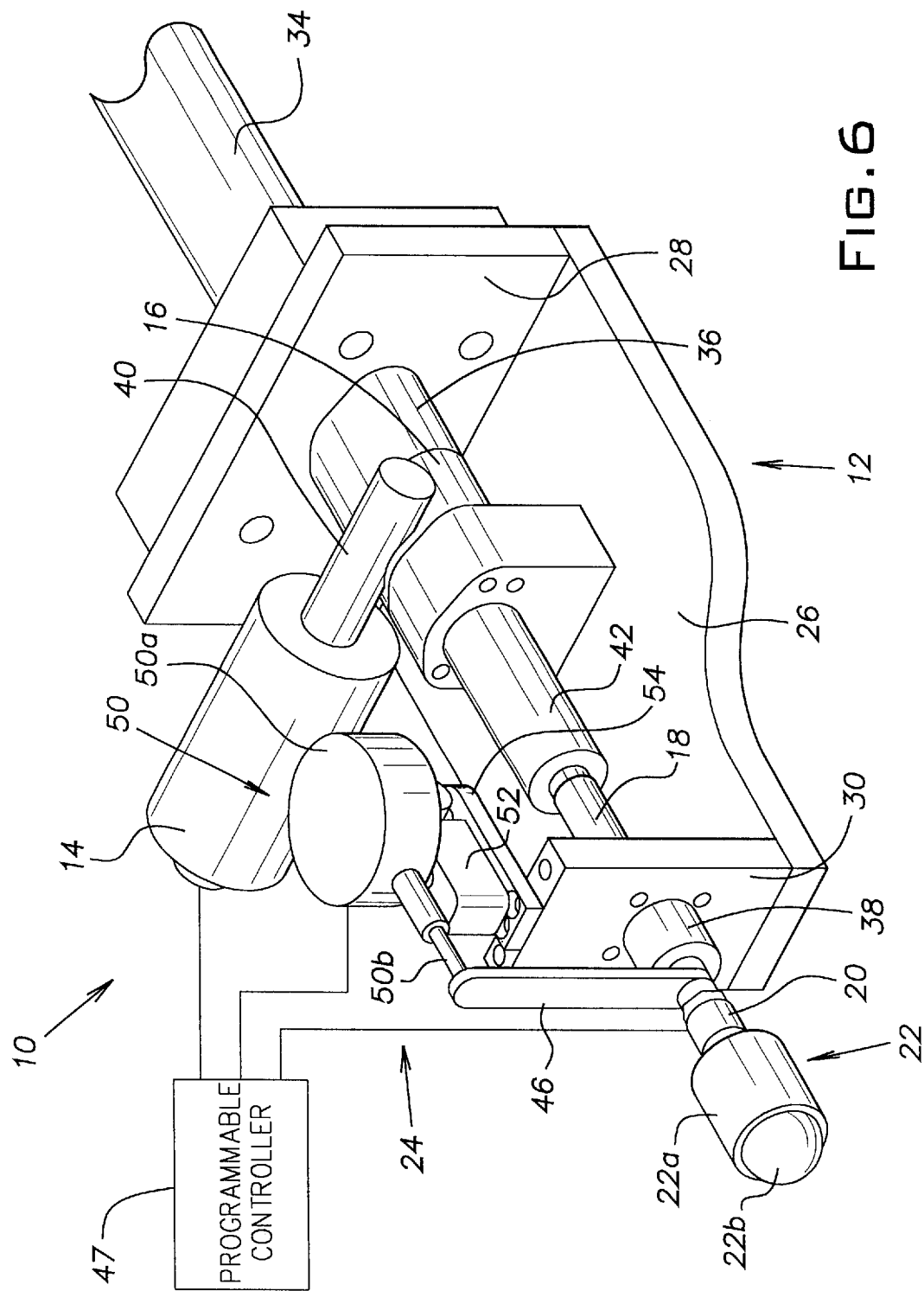

In an automated procedure according to a second preferred embodiment of the present invention illustrated in FIG. 6, the programmable controller 47 controls operation of the motor 14 to move the shaft 18, and the dimple head 22 secured thereto, toward and away from the body panel being tested. The programmable controller 47 monitors the pressure sensed by the load cell 20 and the deflection sensed by the displacement detection assembly 24. Measured data provided by the load cell 20 is used by the programmable controller 47 to control operation of the testing device 10 in a predetermined fashion, notably activation of the motor 14 to move the shaft forward and away from the sheet metal part. The programmable controller 47 monitors the deflection data provided by the displacement measuring device 50 and stores certain data for further analysis, as will be apparent from the following discussion. In a completely automated process, the programmable controller 47 further controls the movement of the robot arm 34 so as to perform a series of testing operations over a predetermined grid of points on a body panel, as will be discussed more fully hereinafter. In any event, measured data will be correlated to specific positions or test points on the body panel being tested and is used to identify areas on the body panel that exhibit weakness to deflection.

To test a body panel (BP, FIG. 5), the body panel contour or shape is input into the programmable controller 47, as well as the spacing between test points, to establish a three dimensional grid of testing points. The robot arm 34 is moved to place the testing device 10 in a position such that the dimple head 22 is adjacent a first desired test point. Thereafter, the programmable controller 47 activates the motor 14 to move the shaft 18 and dimple head 22 toward the body panel test point. The displacement measured by the displacement measuring device 50 when the load cell 20 measures resistance to movement is stored by the programmable controller 47 as the first reference displacement value ($DV_1$, FIG. 5), and the motor continues driving the dimple head into the body panel until the predetermined force (i.e., 20 kg) is measured.

The displacement measured at the predetermined force is stored in the programmable controller 47 as the second reference displacement value ($DV_2$, FIG. 5), with the difference between the first and second displacement values being the maximum deflection ($D_M$, FIG. 5), which is one measure of the body panel's resistance to deformation at the first test point. Thereafter, the programmable controller 47 reverses the motor 14 to move the dimple head 22 away from the body panel. When the programmable controller 47 determines that, based upon displacement information provided by the displacement measuring device 50, the dimple head 22 is moved rearwardly slightly from the first reference displacement value (i.e., the location in which the body panel was first engaged by the dimple head 22), the motor 14 is again reversed to drive the dimple head 22 toward and into the body panel.

Figure 5:
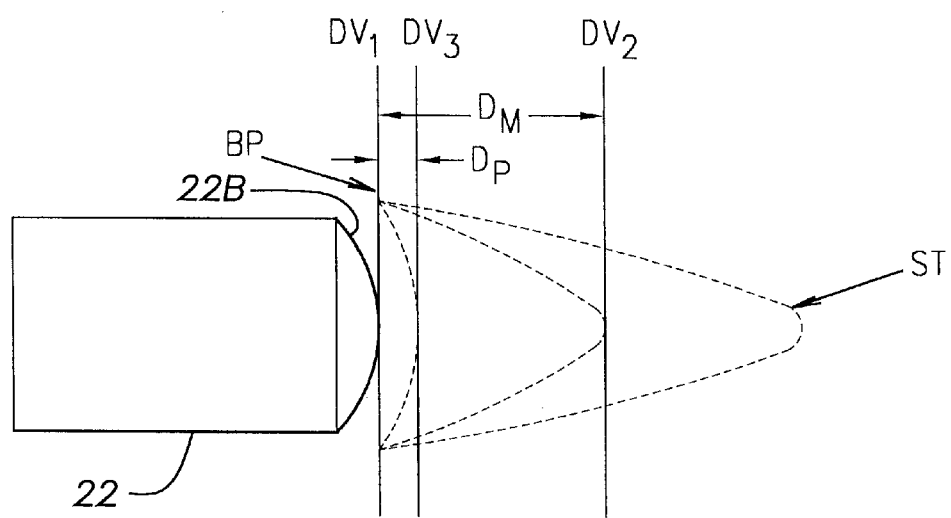
FIG. 5 schematically illustrates deformation of a body panel at different stages of a testing procedure according to the present invention; and, FIG. 6 is a perspective view of a device for testing metal parts according to a second embodiment of the present invention.

As the dimple head 22 is moved toward the body panel, the displacement measured by the displacement measuring device 50 when the load cell 20 detects resistance to movement (i.e., when the dimple head 22 engages the deformed body panel surface) is stored by the programmable controller 47 as the third reference displacement value ($DV_3$, FIG. 5). The programmable controller 47 calculates the difference between the first and third reference displacement values, which is the amount of permanent deformation ($D_P$, FIG. 5) experienced at the body panel first test point due to the predetermined load. The programmable controller 47 stores the permanent deformation measurement to complete the test procedure on the first test point and, thereafter, reverses the motor 14 to move the dimple head 22 away from the body panel. The testing device 10 is then moved to the next test point, either automatically under the guidance of the controller 47 or manually by the operator, and the process is continued in this manner until each of the test points over the entire desired area of the body panel have been tested.

As in the manual testing process of the first embodiment, during the automatic testing procedure the load cell data is monitored to determine whether snap-through or "oil-canning". A sharp drop in pressure sensed by the load cell 20 during initial movement of the dimple head 22 into the body panel (i.e., during application of the predetermined force) is indicative of such snap-through, and will be recorded by the programmable controller 47 as a gross failure (ST, FIG. 5) of the body panel at the subject test point.

In each embodiment, the body panel is preferably sequentially tested over a matrix of test points, and the collected data for each individual test point is stored for further analysis. For example, it may be determined that a series of test points exhibit unsatisfactory resistance to deflection, or unsatisfactory levels of permanent deformation at the predetermined test load. Depending upon the extent of the problem, it may be determined that systematic changes, such as altering the cushion pressure, using a different thickness or grade of sheet metal, adding further supports to the sheet metal body panel, or adjusting the location of the body panel supports, are in order. Alternatively, localized remedial measures, such as applying a stiffening pad to the inner side of the body panel, may be in order. Naturally, a body panel wherein such remedial measures have been taken will be re-tested to assess whether such measures have been successful. Accordingly, the present invention is an important addition to quality control processes that are employed in a manufacturing process, and may also be useful in initial design studies.

While the present invention has been described with particularity herein, it is considered apparent that the present invention is capable of numerous modifications, substitutions, and rearrangements of parts without departing from the scope and spirit of the present invention. Therefore, the invention is not to be limited to the particular preferred embodiments described hereinbefore, but rather is only defined by the claims appended hereto.

What is claimed is:

1. A method for testing a metal part for deformation, comprising the steps of:

moving a dimple head forwardly toward a test point on said metal part;

determining when said dimple head encounters resistance to movement;

measuring displacement of said dimple head when resistance to movement is encountered to establish a first reference displacement value;

moving said dimple head forwardly into said metal part until a predetermined pressure is detected;

after said predetermined pressure is detected, moving said dimple head rearwardly;

measuring displacement of said dimple head as said dimple head is moved rearwardly and, when said displacement is less than or equal to said first reference displacement value, moving said dimple head forwardly;

determining when said dimple head encounters resistance to movement;

measuring displacement of said dimple head when resistance to movement is encountered to establish a second reference displacement value;

calculating a permanent deformation value of said metal part at said test point by subtracting said first reference displacement value from said second reference displacement value.

2. The method according to claim 1, comprising the further steps of:

measuring displacement of said dimple head when said predetermined pressure is detected to establish a third reference displacement value;

calculating a maximum deformation of said metal part at said test point by subtracting said first reference displacement value from said third reference displacement value.

3. The method according to claim 2, comprising the further steps of:

monitoring forces as said dimple head is moved forwardly toward said third reference displacement value and, upon detection of a predetermined drop in pressure, determining that a gross failure of the metal part has occurred.

4. The method according to claim 2, comprising the further step of:

comparing the calculated maximum deformation with a predetermined maximum deformation value to determine whether said metal part is weak at said test point.

5. The method of claim 1, comprising the further step of:

comparing the calculated permanent deformation value with a predetermined permanent deformation value to determine whether said metal part is weak at said test point.

6. A method for sequentially testing a plurality of locations on a metal part for deformation, comprising the steps of:

a) establishing a grid of said test points to be tested;

b) positioning a dimple head adjacent one of said plurality of test points on said metal part;

c) moving the dimple head forwardly toward the test point;

d) determining when said dimple head encounters resistance to movement;

e) measuring displacement of said dimple head when resistance to movement is encountered to establish a first reference displacement value;

f) moving said dimple head forwardly into said metal part until a predetermined force is detected;

g) measuring displacement of said dimple head when said predetermined force is detected to establish a second reference displacement value;

h) calculating a maximum deformation of said metal part at said test point by subtracting said first reference displacement value from said second reference displacement value;

i) after said predetermined force is detected, moving said dimple head rearwardly;

j) measuring displacement of said dimple head as said dimple head is moved rearwardly and, when said displacement is less than or equal to said first reference displacement value, moving said dimple head forwardly;

k) determining when said dimple head encounters resistance to movement;

l) measuring displacement of said dimple head when resistance to movement is encountered to establish a third reference displacement value;

m) calculating permanent deformation of said metal part at said test point by subtracting said first reference displacement value from said third reference displacement value;

n) moving said dimple head into a position adjacent a subsequent one of said plurality of test points; and, o) repeating steps c–n until each of said plurality of test points has been tested.

7. The method according to claim 6, comprising the further steps of:

for each test point, comparing the calculated maximum deformation with a predetermined maximum deformation value to determine whether said metal part is weak at said test point.

8. The method of claim 7, comprising the further step of:

for each test point, comparing the calculated permanent deformation value with a predetermined permanent deformation value to determine whether said metal part is weak at said test point.

9. The method according to claim 6, comprising the further steps of:

for each test point, monitoring forces as said dimple head is moved forwardly toward said second reference displacement value and, upon detection of a predetermined drop in pressure, determining that a gross failure of the metal part has occurred.

\* \* \* \* \*